United States Patent
Ostrick et al.

(10) Patent No.: US 10,670,548 B2
(45) Date of Patent: Jun. 2, 2020

(54) COMPACT SENSOR MODULE FOR A COMBINATION OF PRESSURE, HUMIDITY AND/OR TEMPERATURE SENSORS

(71) Applicant: EPCOS AG, Munich (DE)

(72) Inventors: Bernhard Ostrick, Teltow (DE); Peter Balzer, Berlin (DE)

(73) Assignee: EPCOS AG, Munich (DE)

( * ) Notice: Subject to any disclaimer, the term of this patent is extended or adjusted under 35 U.S.C. 154(b) by 512 days.

(21) Appl. No.: 14/786,492

(22) PCT Filed: Apr. 9, 2014

(86) PCT No.: PCT/EP2014/057171
§ 371 (c)(1),
(2) Date: Oct. 22, 2015

(87) PCT Pub. No.: WO2014/173686
PCT Pub. Date: Oct. 30, 2014

(65) Prior Publication Data
US 2016/0069831 A1    Mar. 10, 2016

(30) Foreign Application Priority Data
Apr. 22, 2013  (DE) .................. 10 2013 104 043

(51) Int. Cl.
*G01N 27/22* (2006.01)
*G01N 33/00* (2006.01)
*G01D 11/24* (2006.01)

(52) U.S. Cl.
CPC ......... *G01N 27/225* (2013.01); *G01D 11/245* (2013.01); *G01N 33/0032* (2013.01)

(58) Field of Classification Search
CPC . G01N 27/225; G01N 33/0032; G01D 11/245
(Continued)

(56) References Cited

U.S. PATENT DOCUMENTS 5,125,275 A   6/1992  Wilda et al.
5,511,418 A   4/1996  Antikainen et al.
(Continued)

FOREIGN PATENT DOCUMENTS

DE   3911812 A1   10/1990
DE   3942664 A1    6/1991
(Continued)

OTHER PUBLICATIONS

"Humidity Sensor Units—CHS Series," TDK Corporation, Jan. 2010, 7 pages.
(Continued)

*Primary Examiner* — Natalie Huls
*Assistant Examiner* — Monica S Young
(74) *Attorney, Agent, or Firm* — Slater Matsil, LLP

(57) ABSTRACT

A sensor module has a first sensor element and a second sensor element. The first sensor element and the second sensor element are accommodated in a common housing of the sensor module. The sensor module includes a conductor structure that comprises an electrode structure and a separate connection structure. The connection structure is connected in an electrically conductive manner to the first sensor element and the electrode structure is allocated to the second sensor element.

9 Claims, 2 Drawing Sheets

(58) Field of Classification Search
USPC .......................................................... 73/29.2
See application file for complete search history.

(56) References Cited

U.S. PATENT DOCUMENTS

| | | | |
|---|---|---|---|
| 6,766,574 B2 | 7/2004 | Mizoguchi et al. | |
| 6,850,859 B1 | 2/2005 | Schuh | |
| 7,385,296 B2 | 6/2008 | Ohta | |
| 7,771,620 B2 | 8/2010 | Chung et al. | |
| 7,775,115 B2 | 8/2010 | Theuss et al. | |
| 9,239,309 B2 | 1/2016 | Niimi et al. | |
| 2006/0037404 A1* | 2/2006 | Watanabe | G01N 27/223 73/714 |
| 2006/0134480 A1 | 6/2006 | Beasley et al. | |
| 2007/0039385 A1* | 2/2007 | Yang | G01N 27/121 73/335.05 |
| 2008/0227235 A1* | 9/2008 | Theuss | B60C 23/0408 438/53 |
| 2013/0269419 A1* | 10/2013 | Etherington | G01F 1/692 73/37 |
| 2014/0102172 A1* | 4/2014 | Daamen | G01N 27/18 73/25.03 |
| 2014/0112510 A1* | 4/2014 | Yang | H04R 1/021 381/332 |
| 2014/0362966 A1* | 12/2014 | Fushimi | G01T 3/006 376/254 |
| 2016/0004283 A1* | 1/2016 | Ganguly | G06F 1/1656 307/118 |
| 2017/0082567 A1* | 3/2017 | O'Brien | G01N 27/225 |

FOREIGN PATENT DOCUMENTS

| | | |
|---|---|---|
| DE | 69427005 T2 | 9/2001 |
| DE | 10124373 A1 | 11/2001 |
| DE | 102005043013 A1 | 3/2006 |
| DE | 102005048486 A1 | 4/2006 |
| DE | 102005000616 A1 | 7/2006 |
| DE | 102005016002 A1 | 10/2006 |
| DE | 602004008330 T2 | 5/2008 |
| DE | 102007012335 A1 | 9/2008 |
| DE | 102010043083 A1 | 5/2012 |
| EP | 1717500 A1 | 11/2006 |
| EP | 2469270 A1 | 6/2012 |
| JP | S62148258 A | 7/1987 |
| JP | H0552795 A | 3/1993 |
| JP | H05203523 A | 8/1993 |
| JP | H109979 A | 1/1998 |
| JP | H03125219 U | 4/2003 |
| JP | 2006058137 A | 3/2006 |
| JP | 2006242776 A | 9/2006 |
| JP | 2007502342 A | 2/2007 |
| JP | 2008159751 A | 7/2008 |
| JP | 2011176049 A | 9/2011 |
| JP | 2012251933 A | 12/2012 |
| WO | 0206808 A1 | 1/2002 |
| WO | 2004048955 A2 | 6/2004 |
| WO | 2005031273 A1 | 4/2005 |
| WO | 2006072492 A1 | 7/2006 |
| WO | 2009015082 A1 | 1/2009 |
| WO | 2009029426 A1 | 3/2009 |

OTHER PUBLICATIONS

"Pressure Sensor for Barometric Measurements in Consumer Applications," EPCOS AG, Product Brief 2011, T5400 Technical Data, Oct. 2011, 2 pages.
"Resistive Type Humidity Sensor," Hokuriku, HDK, Humidity Sensor Model No. HIS-06-N & HIS-08, Humidity Sensor Module Model No. HSU-07 Series & HSU-08 Series, Jul. 11, 2014, 1 page.
Eddy, A.S.G. et al., "Fully Printed Flexible Humidity Sensor," Procedia Engineering, No. 25, Proc. Eurosensors XXV, Athens, Greece, Sep. 4-7, 2011, 4 pages.

* cited by examiner

COMPACT SENSOR MODULE FOR A COMBINATION OF PRESSURE, HUMIDITY AND/OR TEMPERATURE SENSORS

This patent application is a national phase filing under section 371 of PCT/EP2014/057171, filed Apr. 9, 2014, which claims the priority of German patent application 10 2013 104 043.8, filed Apr. 22, 2013, each of which is incorporated herein by reference in its entirety.

TECHNICAL FIELD

The present invention relates to a sensor module and a method for producing the sensor module.

SUMMARY

Embodiments of the invention provide an improved sensor module, in particular a compact sensor module, and also a method for producing the sensor module.

A proposed sensor module comprises a first sensor element and a second sensor element. The first sensor element and the second sensor element are accommodated in a common housing of the sensor module. Furthermore, the sensor module comprises a conductor structure, which comprises an electrode structure, and a connection structure, which is separate from the electrode structure. The connection structure is connected in an electrically conductive manner to the first sensor element. The electrode structure is allocated to the second sensor element. It is advantageous that the proposed sensor module renders it possible to provide a combined sensor module that by way of example in comparison to sensor modules that comprise only one sensor element or a sensor detects a plurality of measurement variables and also in comparison to a plurality of individual sensor elements renders it possible to produce a compact design that requires little installation space. Furthermore, the proposed module renders it possible to maintain the outlay advantageously low with regard to the production process for providing the first and/or the second sensor element in the housing.

In one preferred embodiment, the sensor module is a climate sensor module. This embodiment supports an integration of the first sensor element and the second sensor element in a common housing since the two sensor elements can require a comparable connection to or a comparable interface with the environment or the medium, by way of example air, that surrounds the sensor module. For example, the first sensor element or the second sensor element can be a pressure sensor for measuring the air pressure and the other sensor element can be a humidity sensor for measuring the air humidity. Furthermore, the embodiment as a climate sensor module supports the compact design of the sensor module.

In one embodiment, the connection structure is spaced apart from the electrode structure. This embodiment renders it possible in an advantageous manner to use the connection structure and the electrode structure for difference purposes during the operation of the sensor module.

In one embodiment, the connection structure comprises an external connection. The external connection is connected in an electrically conductive manner to the connection structure. It is preferred that the external connection represents an external electrical connection of the sensor module to the connection structure. The external connection can penetrate the housing of the sensor element in order to be accessible from outside the sensor module. It is possible in an advantageous manner by way of the external connection to transmit a measured variable of the first sensor element from the sensor module.

In one embodiment, the electrode structure comprises an external connection that is connected in an electrically conductive manner to the electrode structure. The external connection of the electrode structure can be embodied in a similar manner to the external connection of the connection structure in order by way of example to transmit a measured variable of the second sensor element.

In one preferred embodiment, the first sensor element is embodied so as to detect a first measured variable by way of example the ambient pressure or air pressure, or a variable from which it is possible to ascertain the ambient pressure or air pressure.

In one preferred embodiment, the second sensor element can be embodied so as to detect a second measured variable, by way of example the relative humidity or the air humidity, or a variable from which it is possible to ascertain the relative humidity or the air humidity.

Alternatively, the second sensor element can be embodied so that the second measured variable represents a gas concentration or the percentage portion of a gas, by way of example in an environment or gas atmosphere of the sensor module.

In one preferred embodiment, the electrode structure is part of the second sensor element. In accordance with this embodiment, the second measured variable can be ascertained in an advantageous manner by way of the electrical characteristics of the electrode structure.

In one preferred embodiment, the electrode structure is provided with a coating. Furthermore, a measuring principle of the second sensor element relates to an interaction of the electrode structure with the coating. The coating renders it possible in an advantageous manner for the electrical characteristics of the electrode structure to be changed, by way of example by way of the air humidity.

In one embodiment, the electrode structure comprises electrodes that are electrically separate one from the other and that interdigitate one in the other. Furthermore, the measuring principle of the second sensor element is a capacitive measuring principle. It is preferred that during the operation of the sensor module different interdigitated electrodes are allocated to different electrical polarities. The second measured variable is detected by way of example by way of a change in the electrical capacity that is formed by way of example after applying an electrical measuring voltage between the interdigitated electrodes. The electrical measuring voltage can be applied to the electrode structure by way of example by way of the external connection of the electrode structure.

It is preferred that the coating is or comprises a polymer, by way of example polyimide, in order to form a dielectric of a capacitor that is formed by means of the interdigitated electrodes. After the coating has been applied, the coating is located in an expedient manner between the electrodes in order to form the dielectric and also above the electrodes.

It is preferred that the coating absorbs or dissipates moisture from the air or the environment in dependence upon the relative humidity, ambient humidity or air humidity so that the capacity of the capacitor changes. The coating can absorb moisture from or dissipate moisture to the air or the environment in accordance with a power law. Furthermore, it is possible by way of a change in the capacity to ascertain by way of example a change in the ambient humidity or air humidity of an electronic unit.

In one embodiment, the measuring principle of the second sensor element is a resistive measuring principle. In accordance with this embodiment, the electrode structure is embodied in an expedient manner in conjunction with or rather only with one electrode. It is preferred that the second measured variable is detected by way of a change in the electrical resistance of the electrode structure. Furthermore, the change in the electrical resistance and/or the electrical conductance can be ascertained by the electronic unit by way of example by way of a change in the ambient humidity or air humidity.

The electronic unit can be a signal processing unit of the sensor module or an external unit that is supplied by way of example by way of the external connection of the electrode structure and/or by way of the external connection of the connection structure to the first and/or the second measured variable.

In one preferred embodiment, the housing defines an inner chamber having internal surfaces, wherein the connection structure and the electrode structure are arranged on the same internal surface or different internal surfaces. In accordance with one embodiment, the connection structure and the electrode structure during the operation of the sensor module are advantageously protected with respect to external influences. It is preferred that one internal surface describes a surface on an inner face of the housing.

In one preferred embodiment, the sensor module comprises a first housing part and a second housing part that are connected so as to form the housing of the sensor module. This embodiment renders it possible in an advantageous manner to facilitate providing the housing by way of example with the first sensor element. Furthermore, it is possible in this manner to simplify the entire production process of the sensor module.

The first housing part can be a housing body and the second housing part can be a housing cover, or conversely.

In one preferred embodiment, the first and/or the second housing part comprise a ventilation aperture. It is possible by way of the ventilation aperture in an advantageous manner to connect the first and/or the second sensor element to the environment, in particular to the air that is surrounding the sensor element or to a gas atmosphere that is surrounding the sensor element. This is in particular expedient when the sensor module is embodied as a climate sensor module.

In one preferred embodiment, the first housing part and the second housing part each comprise a multi-layer ceramic assembly. In accordance with this embodiment, the sensor module can be provided in an advantageous manner with the connection structure and the electrode structure in such a manner that during the operation of the sensor module heat by way of example Joule heat that is generated by means of the connection structure and/or by means of the electrode structure can be dissipated in an advantageous manner. Furthermore, the sensor module can be produced in accordance with this embodiment in a particularly compact manner with multi-layer ceramic assemblies and also by way of example can be protected against external electrical fields.

In one preferred embodiment, the first housing part comprises a hybrid ceramic assembly or circuit board and the second housing part has a metal characteristic, or conversely. It is preferred that the first or the second housing part in accordance with this embodiment is embodied from metal or comprises a metal. Furthermore, the first or the second housing part can be manufactured from a material that has metallic characteristics. This housing part can form a cap or a cover of the sensor module, whereas it is preferred that the housing part that comprises the hybrid ceramic assembly or the circuit board represents a housing body.

In one embodiment, the first housing part and the second housing part comprises in each case an injection-molded material.

In comparison to the injection-molded embodiment of the first and the second housing part, the embodiment of the first and the second housing part that is embodied as a multi-layer ceramic assembly has the advantage of a more compact design of the sensor module.

In one embodiment, the connection structure and/or the electrode structure is embodied in a planar manner.

In one embodiment, the conductor structure is embodied in a planar manner.

In one embodiment, the connection structure and/or the electrode structure is embodied in a three-dimensional manner.

The embodiments of the first and of the second housing part that comprise a multi-layer ceramic assembly or rather the injection-molded material render it possible in an advantageous manner to design the first and/or the second housing part as three-dimensional circuit carriers or as a three-dimensional circuit.

In one preferred embodiment, the sensor module comprises a signal processing unit that is embodied so as to ascertain from the first and/or the second measured variable a derived variable by way of example the water vapor partial pressure or the humidity partial pressure. A further derived variable can be the air density. The signal processing unit can be embodied as an alternative or in addition thereto so as in the first instance to ascertain the first and/or the second measured variable or so as to contribute to the variables being ascertained.

By virtue of integrating the signal processing unit in the sensor module, the derived variable can be transmitted in an advantageous manner directly by the sensor module, and consequently it is possible to forego an external electronic unit or a further signal processing module that is separate from the sensor module. The signal processing unit can comprise an external connection similar to the electrode structure and to the connection structure so that a derived variable can be transmitted by the sensor module by way of the external connection. The signal processing unit is advantageously connected in an electrically conductive manner to the connection structure and the electrode structure so that in the case of the signal processing unit being provided it is possible to forego external connections of the electrode structure and the connection structure.

In one preferred embodiment, the sensor module comprises a temperature sensor, by way of example for measuring the ambient temperature. The temperature sensor can be connected in an electrically conductive manner to the signal processing unit. Furthermore, a temperature, for example, the ambient temperature that is measured by the temperature sensor can be transmitted in this manner to the signal processing unit. It is preferred that the signal processing unit is suitable to use a measured value of the temperature sensor for ascertaining a variable that is derived from the first and/or the second measured value.

The temperature sensor can also be embodied as part of the signal processing unit. Furthermore, the temperature sensor concerned can be a diode.

In one preferred embodiment, the conductor structure is embodied in such a manner that either the first housing part or the second housing part is provided with the electrode structure and the connection structure. In accordance with this embodiment, by way of example the housing part that is not provided with the electrode structure and the connection structure has sufficient space for the signal processing unit so that a compact design of the sensor module can be achieved.

In one embodiment, the conductor structure is embodied in such a manner that the first housing part is provided with the electrode structure and the second housing part is provided with the connection structure, or conversely. This embodiment likewise renders it advantageously possible to achieve a compact design of the sensor module since the connection structure and the electrode structure in accordance with this embodiment are not provided with one and the same housing part.

In accordance with this embodiment, it is preferred that the first sensor element is arranged on the housing part that is provided with the connection structure.

Furthermore, a method is proposed for producing the sensor element. The method includes providing the first housing part and the second housing part, wherein the first housing part and the second housing part are embodied so as to form a housing of the sensor module. Furthermore, the method includes providing the first housing part or the two housing parts with the conductor structure. The first housing part or the two housing parts can be provided with the conductor structure by way of example by way of the same lithographic steps or in a common deposition process. The conductor structure comprises the electrode structure and the connection structure that is electrically separate from the electrode structure. In one method step either the first housing part is provided with the electrode structure and the connection structure or in one method step the first housing part is provided with the connection structure and the second housing part is provided with the electrode structure in order to connect the first and the second sensor element in an electrically conductive manner to the conductor structure. Furthermore, the method includes providing the housing with the first sensor element. Furthermore, the method includes producing the sensor module. The process of producing the sensor module can include mounting and/or assembling the first and the second housing part.

In one embodiment of the method, the first or the second housing part is provided with the electrode structure and connection structure in order to connect the first and the second sensor element in an electrically conductive manner to the conductor structure.

In one embodiment of the method, the first housing part is provided with the connection structure and the second housing part is provided with the electrode structure, or conversely, in order to connect the first and the second sensor element in an electrically conductive manner to the conductor structure.

One advantage of the proposed method relates to the possibility of providing the housing in one and the same method step with the conductor structure, including the electrode structure and the connection structure.

It is preferred that the sensor module can be produced or is produced by means of the method described herein. In particular, all the features that are disclosed for the method are also disclosed for the sensor module, and conversely.

In one preferred embodiment of the method, the housing part that is provided with the connection structure is provided with the first sensor element. This embodiment renders it possible to provide the electrically conductive connection between the first sensor element and the connection structure in a particularly simple manner.

In one preferred embodiment of the method, the electrode structure is provided with the coating in order to form the second sensor element.

In one preferred embodiment, the sensor module or rather the housing has a length between 2.5 mm and 5 mm.

In one preferred embodiment, the sensor element or rather the housing has a width between 2.5 mm and 5 mm.

In one preferred embodiment, the sensor module or rather the housing has and a height between 0.2 mm and 2 mm.

BRIEF DESCRIPTION OF THE DRAWINGS

Further advantage, advantageous embodiments and purposes of the invention are disclosed in the following description of the exemplary embodiments in conjunction with the figures.

Figure 1A:
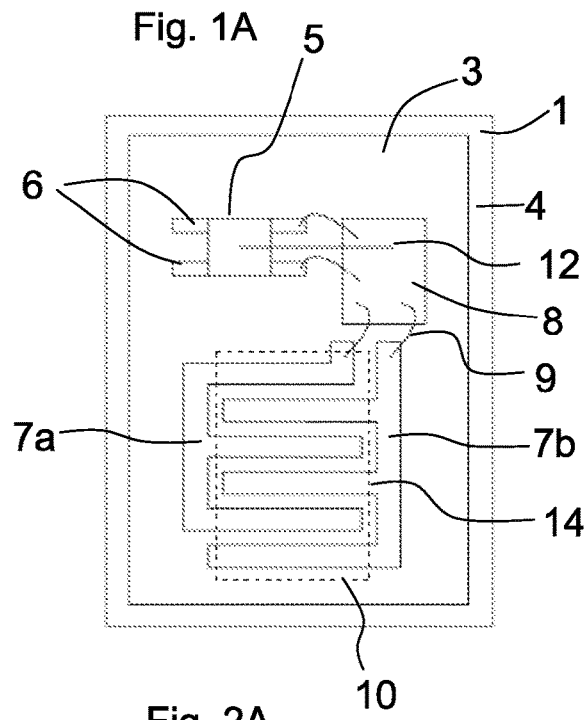
FIG. 1A illustrates a schematic view of an inner face of a first housing part.

Like, like-type and like-functioning elements are provided in the figures with like reference numerals. The figures and the size ratios of the elements illustrated in the figures are not to be regarded as being to scale. On the contrary, individual elements are represented in a disproportionally large manner in order to improve the presentability and/or to improve the understanding of the invention.

DETAILED DESCRIPTION OF ILLUSTRATIVE EMBODIMENTS

FIG. 1A illustrates a first housing part 1. The first housing part 1 is part of a housing of a sensor module. The first housing part 1 comprises a border 4. Furthermore, the first housing part 1 comprises an internal surface or inner face 3. The first housing part 1 is provided with a connection structure 6. Furthermore, a first sensor element 5 is arranged on or fixed to the inner face 3 of the first housing part 1. The first sensor element 5 is connected in an electrically conductive manner to the connection structure 6. It is preferred that the first sensor element 5 is embodied so as to ascertain a first measured variable. It is preferred that this first measured variable is the air pressure of the environment of the sensor element. It is preferred that the first sensor module 5 is an air pressure sensor. The connection structure 6 can comprise one or multiple external connections (not explicitly illustrated) by way of example for transmitting the first measured variable from the sensor module.

Furthermore, the first housing part 1 is provided with an electrode structure 7. The electrode structure 7 and the connection structure 6 form a conductor structure (not explicitly illustrated), in particular an electric conductor structure, of the sensor module. The electrode structure 7 illustrated in FIG. 1A comprises interdigitated electrodes 7a and 7b that are electrically separate from one another. The two interdigitated electrodes can be allocated during the operation of sensor module to different electrical polarities and form a capacitor. An electrical field can be applied to the electrodes 7a and 7b by way of example by way of one or multiple external connections (not explicitly illustrated) of these electrodes.

Furthermore, the electrode structure 7 is provided or coated at least in part with a coating 10. It is preferred that the electrode structure 7 and the coating 10 form a second sensor element 14. It is preferred that the second sensor element is embodied so as to ascertain a second measured variable. It is preferred that the second measured variable is the relative humidity or air humidity of the air or rather of the gas atmosphere that surrounds the sensor module. It is preferred that the second sensor module 14 is a humidity sensor. Alternatively, the second sensor module 14 is a gas sensor and the second measured variable is by way of example a gas concentration or the percentage portion of a gas in the air or in the gas atmosphere surrounding the sensor module.

The coating 10 is located above and in an expedient manner also between the electrodes 7a and 7b in order to form a dielectric of the capacitor that is formed by means of the interdigitated electrodes.

The coating 10 can comprise a polymer, by way of example a polyimide, or can be embodied therefrom. It is preferred that the coating 10 absorbs or dissipates moisture in dependence upon the ambient relative humidity or air relative humidity of the sensor module. The coating 10 can absorb moisture from or dissipate moisture to the air or the environment in accordance with a mathematical power law. The second measured variable can be ascertained by way of a change in the electrical capacity of the interdigitated electrodes in that the capacity of the capacitor that is formed by means of the electrodes 7a and 7b changes by way of example in dependence upon the air humidity. Furthermore, this capacity change can be ascertained by a signal processing unit (see below) of the sensor module.

Furthermore, a signal processing unit 8 is arranged on the inner face 3 of the first housing part 1. The signal processing unit 8 is connected by way of an electrical connection 12 to the first sensor module 5. By way of the electrical connection 12, it is possible by way of example for the first measured variable of the first sensor element 5 to be transmitted electrically to the signal processing unit 8. The first sensor element 5 and also the electrodes 7a and 7b can be connected in an electrically conductive manner as an alternative or in addition thereto by way of bond wires 9 (see, e.g., FIG. 1A) to the signal processing unit 8, by way of example in order to transmit the second measured variable to the signal processing unit. It is preferred that the signal processing unit 8 is embodied so as to ascertain from the first and/or the second measured variable a derived variable, by way of example the water vapor partial pressure or humidity partial pressure. A further derived variable can be the air density. For the purpose of outputting the derived variable by means of the sensor module, the signal processing unit 8 can comprise one or multiple external (not explicitly illustrated) electrical connections.

It is preferred that the signal processing unit 8 is suitable to use a measuring value of a temperature sensor (not explicitly illustrated) of the sensor module for determining a derived variable. The temperature sensor can also be embodied as part of the signal processing unit. The temperature sensor concerned is a semi-conductor device, by way of example a diode. The signal processing unit 8 can be embodied as an alternative or in addition thereto so as in the first instance to ascertain the first and/or the second measured variable or so as to contribute to the variables being ascertained.

The first housing part 1 and the second housing part 2 can comprise in each case a multi-layer ceramic assembly or can be embodied therefrom. Furthermore, the first or the second housing part 1, 2 can comprise a hybrid ceramic assembly or a circuit board and the respective other housing part 2, 1 can comprise a metal or have a metal characteristic. Furthermore, the first and the second housing part can comprise in each case an injection-molded material.

Figure 1B:
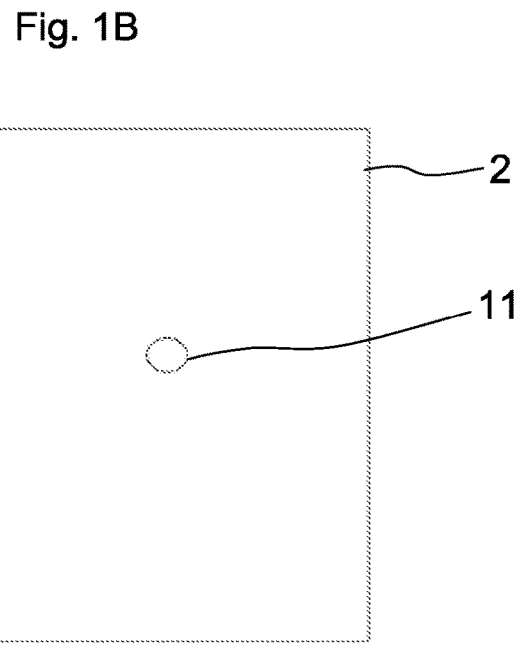
FIG. 1B illustrates a schematic view of a second housing part.

FIG. 1B illustrates a schematic view of a second housing part 2. It is preferred that the second housing part 2 and the first housing part 1 that is illustrated in FIG. 1A form the housing of the described sensor module (not explicitly identified). After the first housing part 1 that is illustrated in FIG. 1A including its components has been provided with the second housing part 2 that is illustrated in FIG. 1B or after the housing parts have been assembled, it is preferred that the described sensor module is formed. It is preferred that this sensor module is a climate sensor module.

The second housing part 2 comprises a ventilation aperture 11. It is possible by way of the ventilation aperture 11 to connect the first and/or the second sensor element 5, 14 to the environment, in particular to the air.

Figure 2A:
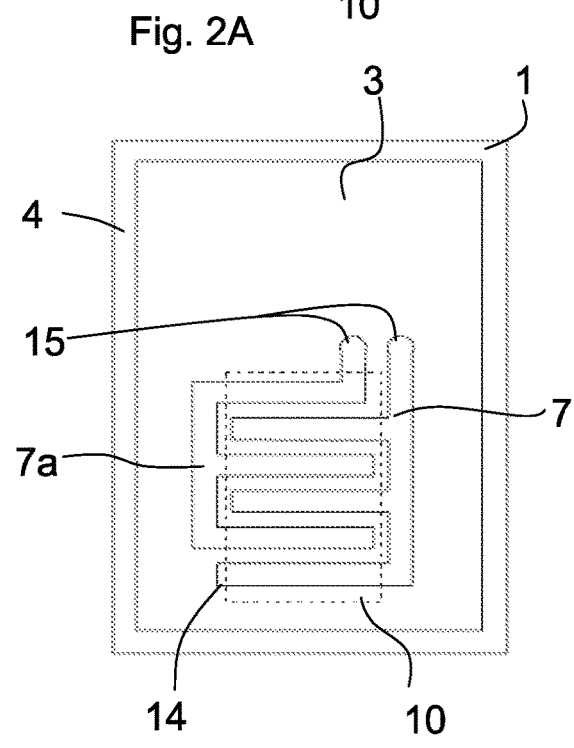
FIG. 2A illustrates a schematic view of an inner face of the first housing part according to an alternative embodiment of the sensor module.

FIG. 2A illustrates an alternative embodiment of a first housing part of the sensor module. The second housing part 2 is provided with the electrode structure 7. In contrast to FIG. 1A, the first housing part 1 comprises merely the second sensor element 14 having the electrode structure 7 and the coating 10. The second sensor element 14 is likewise arranged on the inner face 3 of the first housing part 1.

Figure 2B:
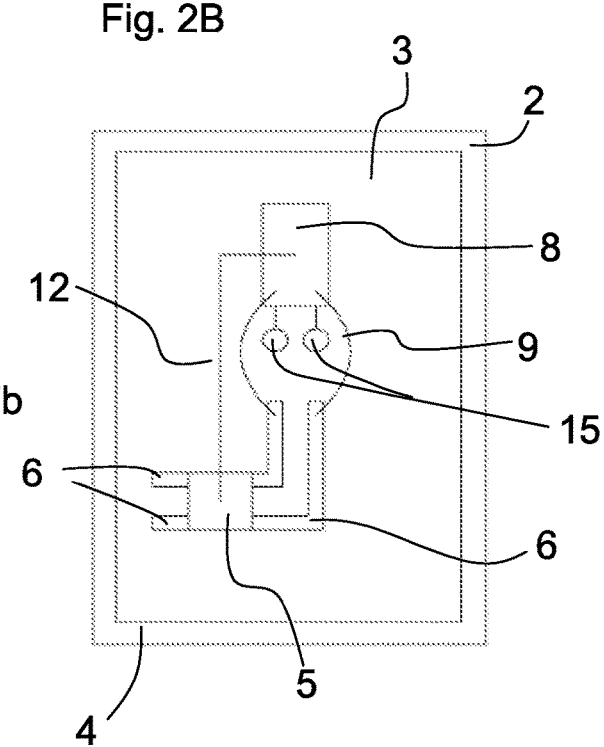
FIG. 2B illustrates in accordance with the embodiment illustrated in FIG. 2A a schematic view of an inner face of a second housing part of the sensor module.

FIG. 2B illustrates a schematic view of an inner face 3 of the second housing part 2. The second housing part 2 is provided with the connection structure 6. The connection structure 6, the first sensor element 5 and the signal processing unit 8 are arranged in FIG. 2B on an inner face 3 of the second housing part 2.

Figure 3:
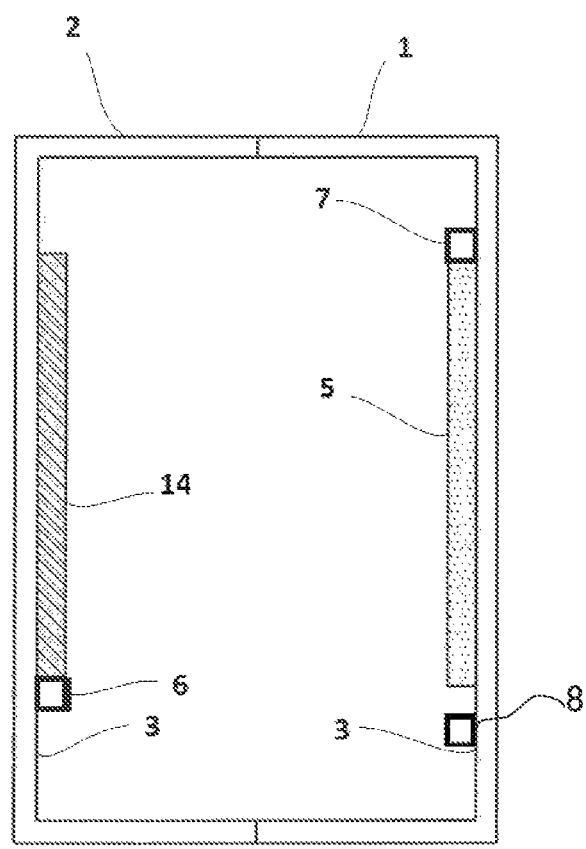
FIG. 3 illustrates in accordance with the embodiment illustrated in FIGS. 2A and 2B, a schematic view of a first housing part and a second housing part of the sensor module.

FIG. 3 illustrates a schematic view of the first housing part 1 being connected to the second housing part 2. As illustrated, inner surface 3 of the first housing part 1 is where second sensor element 14 having electrode structure 7 is arranged. Inner surface 3 of the second housing part 2 is different from inner surface 3 of the first housing part 1. The inner surface 3 of the second housing part 2 is where first sensor element 5 with connection structure 6 are arranged.

Furthermore, the first sensor element 5 and the signal processing unit 8 are connected in an electrically conductive manner to one another by way of the electrical connection 12. Furthermore, the connection structure 6 is connected in an electrically conductive manner to the signal processing unit 8 by way of the bond wires 9.

FIG. 2A and FIG. 2B illustrate in an exemplary manner in each case two connection points 15. It is possible by way of the connection points 15 after the first housing part 1 and the second housing part 2 have been assembled or mounted to connect the electrode structure 7 in an electrically conductive manner preferably to the signal processing unit 8 so that by way of example a second measured variable can be transmitted to the signal processing unit 8. The connection points 15 can be integrated by way of example in part as conductor tracks in the multi-layer ceramic assembly or in the injection-molded housing parts 1 and 2. The first housing part 1 and the second housing part 2 are preferably welded or soldered by way of the connection points 15 for the mounting process. The connection points can also be arranged in a different manner to that illustrated in the figures on the border 4 of the first or the second housing part in order to facilitate the mounting process.

Alternatively to the described electrode structure 7, the electrode structure can likewise comprise only one electrode that together with a corresponding coating forms the second sensor element 14. The coating can likewise be formed by means of a polymer or can comprise such a polymer. In accordance with this embodiment, the measuring principle of the second sensor element can be a resistive measuring principle, wherein the second measured variable is ascertained by way of the change in the electrical resistance and/or in the electrical conductance by way of example in dependence upon the air humidity.

The connection or the external connections of the connection structure, of the electrode structure and/or of the signal processing unit can comprise in each case a through-connection from the inner face of the first or second housing part to a corresponding outer face.

In order to produce the sensor module, the first and the second housing part are provided in the first instance and the housing parts are provided in accordance with the illustrated arrangements or embodiments in one method step with the conductor structure. The first housing part or the two housing parts can be provided with the conductor structure by way of example by way of the same lithographic steps or in a common sputter or deposition process. Accordingly, the connection structure and the electrode structure can be embodied in an expedient manner from the same material. Furthermore, the housing can be provided with the first sensor element and the sensor module can be assembled and produced.

The invention is not limited by the description with reference to the exemplary embodiments. On the contrary, the invention includes any new feature and also any combination of features which includes in particular each combination of features in the claims even if this feature or this combination itself is not explicitly disclosed in the claims or exemplary embodiments.

The invention claimed is:

1. A sensor module comprising:
a housing that comprises a first housing part, and a second housing part connected to the first housing part;
a first climate sensor located in the housing, wherein the first climate sensor is configured to detect a measurement of a first variable related to environmental sensing;
a second climate sensor located in the housing, wherein the second climate sensor is configured to detect a measurement of a second variable related to environmental sensing, wherein the second variable is different from the first variable;
a signal processor located in the housing, wherein the signal processor is configured to ascertain a derived variable from the first variable and the second variable; and
a conductor structure that comprises an electrode structure and an electrical connection structure that is separate from the electrode structure, wherein the electrical connection structure is electrically connected to the first climate sensor and the electrode structure is allocated to the second climate sensor,
wherein the first housing part and the second housing part define an internal chamber of the housing, wherein the internal chamber has a plurality of internal surfaces,
wherein internal surfaces in the first housing part are different from internal surfaces in the second housing part,
wherein the electrical connection structure and the electrode structure are arranged on different internal surfaces of the plurality of internal surfaces,
wherein the electrode structure is spaced apart from the electrical connection structure
wherein the electrode structure is disposed in the first housing part, and the electrical connection structure and the signal processor are disposed in the second housing part, and
wherein the conductor structure for the electrode structure and the electrical connection structure arranged at the first and second housing parts are formed by the same lithographic steps or in a common sputtering or deposition process.

2. The sensor module according to claim 1, wherein the first climate sensor comprises a pressure sensor and the second climate sensor comprises a humidity sensor.

3. The sensor module according to claim 2, wherein the signal processor configured to ascertain water vapor partial pressure or humidity partial pressure.

4. The sensor module according to claim 1, wherein the electrode structure is part of the second climate sensor.

5. The sensor module according to claim 4, wherein the electrode structure is provided with a coating, and wherein a measuring principle of the second climate sensor relates to an interaction of the electrode structure with the coating.

6. The sensor module according to claim 5, wherein the electrode structure comprises interdigitated electrodes that are electrically separate from one another, and wherein the measuring principle of the second climate sensor is a capacitive measuring principle.

7. The sensor module according to claim 5, wherein the measuring principle of the second climate sensor is a resistive measuring principle.

8. The sensor module according to claim 1, wherein the first housing part or the second housing part comprises a ventilation aperture.

9. The sensor module according to claim 1, wherein the first housing part and the second housing part each comprises a multi-layer ceramic assembly.

* * * * *